(12) United States Patent
Yang et al.

(10) Patent No.: US 10,094,776 B2
(45) Date of Patent: Oct. 9, 2018

(54) DUST SENSOR WITH MASS SEPARATION FLUID CHANNELS AND FAN CONTROL

(71) Applicant: Honeywell International Inc., Morris Plains, NJ (US)

(72) Inventors: Ouyang Yang, Shanghai (CN); Kevin Cai, Shanghai (CN); Kai Huang, Shanghai (CN)

(73) Assignee: Honeywell International Inc., Morris Plains, NJ (US)

( * ) Notice: Subject to any disclaimer, the term of this patent is extended or adjusted under 35 U.S.C. 154(b) by 143 days.

(21) Appl. No.: 15/213,139

(22) Filed: Jul. 18, 2016

(65) Prior Publication Data

US 2018/0017488 A1    Jan. 18, 2018

(51) Int. Cl.
*G01N 21/53* (2006.01)
*G01N 15/02* (2006.01)
(Continued)

(52) U.S. Cl.
CPC ......... *G01N 21/53* (2013.01); *G01N 15/0205* (2013.01); *G01N 15/0255* (2013.01);
(Continued)

(58) Field of Classification Search
CPC ... G01N 2015/0046; G01N 2015/0096; G01N 2015/0216; G01N 2015/0222;
(Continued)

(56) References Cited

U.S. PATENT DOCUMENTS

| | | | | |
|---|---|---|---|---|
| 3,787,122 A | * | 1/1974 | Lepper, Jr. ............. | G01N 21/53 250/574 |
| 3,952,207 A | * | 4/1976 | Leschonski ........ | G01N 15/0255 250/573 |

(Continued)

FOREIGN PATENT DOCUMENTS

| | | |
|---|---|---|
| CN | 1800820 A | 7/2006 |
| CN | 104316443 A | 1/2015 |

(Continued)

OTHER PUBLICATIONS

International Application No. PCT/CN2015/097546, International Search Report, dated Sep. 6, 2016, 4 pages.

(Continued)

*Primary Examiner* — Gordon J Stock, Jr.
(74) *Attorney, Agent, or Firm* — Craige Thompson; Thompson Patent Law

(57) ABSTRACT

A particulate matter (PM) sensor. The sensor comprises a mass separation fluid tunnel body defining a fluid inflow channel, a first fluid channel branch opening off of the inflow channel and having a first outlet, a second fluid channel branch opening off of the inflow channel and having a second outlet, and a fluid port between the first fluid channel branch and the second fluid channel branch, a fan located downstream of the first outlet and the second outlet, a photodetector located in the first fluid channel branch, and a computing device coupled to the photodetector having a processor and a memory storing instructions which, when executed by the processor, determines a mass concentration (Continued)

of particles in the first fluid channel branch based on an output of the photodetector.

13 Claims, 4 Drawing Sheets

(51) Int. Cl.
　　*G01N 15/06*　　(2006.01)
　　*G01N 15/00*　　(2006.01)
(52) U.S. Cl.
　　CPC ..... *G01N 15/06* (2013.01); *G01N 2015/0046* (2013.01); *G01N 2015/0288* (2013.01); *G01N 2015/0693* (2013.01)
(58) Field of Classification Search
　　CPC ... G01N 2015/0233; G01N 2015/0238; G01N 2015/0261; G01N 2015/0277; G01N 2015/0283; G01N 2015/0288; G01N 2015/0294; G01N 2015/03; G01N 2015/035; G01N 2015/0681; G01N 2015/0693; G01N 15/02; G01N 15/0205; G01N 15/0211; G01N 15/0227; G01N 15/0255; G01N 15/0272; G01N 15/06; G01N 15/0606; G01N 15/0612; G01N 15/0618; G01N 15/0625; G01N 21/47; G01N 21/49; G01N 21/53; G01N 21/534; G08B 17/10; G08B 17/103; G08B 17/107
　　See application file for complete search history.

(56) References Cited

U.S. PATENT DOCUMENTS

| | | | | |
|---|---|---|---|---|
| 4,197,013 | A * | 4/1980 | Van Ackeren | G01N 21/534 250/252.1 |
| 4,223,559 | A * | 9/1980 | Chuan | G08B 17/12 340/627 |
| 5,420,440 | A * | 5/1995 | Ketler | G01N 21/534 250/573 |
| 5,426,501 | A | 6/1995 | Hokanson et al. | |
| 7,049,824 | B2 * | 5/2006 | Shabino | G01N 1/06 324/464 |
| 7,927,408 | B2 | 4/2011 | Sheoran et al. | |
| 8,243,274 | B2 | 8/2012 | Aiken et al. | |
| 8,813,540 | B2 * | 8/2014 | Dantler | G01N 1/14 340/627 |
| 9,805,570 | B2 * | 10/2017 | Alexander | G08B 29/24 |
| 2004/0159799 | A1 | 8/2004 | Saccomanno | |
| 2008/0156187 | A1 * | 7/2008 | Tingle | F02C 7/052 95/22 |
| 2010/0172471 | A1 * | 7/2010 | Sivathanu | G01N 9/24 378/54 |
| 2010/0269600 | A1 * | 10/2010 | Marra | G01N 15/0266 73/865.5 |
| 2010/0288921 | A1 * | 11/2010 | Wang | G01N 15/0205 250/287 |
| 2013/0195245 | A1 * | 8/2013 | Sivathanu | G01N 23/04 378/54 |
| 2015/0253165 | A1 * | 9/2015 | Ajay | G01F 1/66 73/28.01 |
| 2016/0349168 | A1 * | 12/2016 | Takasu | G01N 15/06 |

FOREIGN PATENT DOCUMENTS

| | | |
|---|---|---|
| CN | 204613066 U | 9/2015 |
| WO | 2015008519 A1 | 1/2015 |
| WO | 2015087583 A1 | 6/2015 |
| WO | 2017101038 A1 | 6/2017 |

OTHER PUBLICATIONS

International Application No. PCT/CN2015/097546, Written Opinion of the International Searching Authority, dated Sep. 6, 2016, 4 pages.

* cited by examiner

DUST SENSOR WITH MASS SEPARATION FLUID CHANNELS AND FAN CONTROL

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

A particulate matter sensor or dust sensor may be used to determine a quality of air, for example in a quality of air that is input to and/or output from an air cleaner. In some industrialized regions, environmental air may have high concentrations of particulate matter of different sizes. If the concentration of such particulate matter is high enough, it may be deleterious to human health. Consumers may wish to purchase and install air cleaners for the residences to improve the quality of air breathed in the home. Such consumer grade air cleaners may desirably be modestly priced and compact in size.

SUMMARY

In an embodiment, a particulate matter (PM) sensor is disclosed. The sensor comprises a mass separation fluid tunnel body defining a fluid inflow channel, a first fluid channel branch opening off of the inflow channel and having a first outlet, a second fluid channel branch opening off of the inflow channel and having a second outlet, and a fluid port between the first fluid channel branch and the second fluid channel branch, a fan located downstream of the first outlet and the second outlet, a photodetector located in the first fluid channel branch, and a computing device coupled to the photodetector having a processor and a memory storing instructions which, when executed by the processor, determines a mass concentration of particles in the first fluid channel branch based on an output of the photodetector.

In another embodiment, a particulate matter (PM) sensor is disclosed. The particulate matter sensor comprises a mass separation fluid tunnel body defining a fluid inflow channel, a first fluid channel branch opening off of the inflow channel and having a first outlet, and a second fluid channel branch opening off of the inflow channel and having a second outlet, a fan located downstream of the first outlet, an adjustable speed fan located downstream of the second outlet, a photodetector located in the first fluid channel branch, and a computing device coupled to the photodetector having a processor and a memory storing instructions which, when executed by the processor, controls the speed of the adjustable speed fan based on a fan speed parameter stored in the memory and determines a mass concentration of particles in the first fluid channel branch based on an output of the photodetector.

In yet another embodiment, a particulate matter (PM) sensor is disclosed. The particulate matter sensor comprises a mass separation fluid tunnel body defining a fluid inflow channel, a first fluid channel branch opening off of the inflow channel and having a first outlet, a second fluid channel branch opening off of the inflow channel and having a second outlet, and a fluid port between the first fluid channel branch and the second fluid channel branch, a fan located downstream of the first outlet and the second outlet, a laser diode, a photodetector located in the first fluid channel branch, and a computing device coupled to the photodetector having a processor and a memory storing instructions which, when executed by the processor, determines a mass concentration of particles in the first fluid channel branch based on an output of the photodetector, where the output of the photodetector is based on detecting light emitted by the laser diode scattered by dust particles present in a fluid flow through the first fluid channel branch.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

Figure 1:
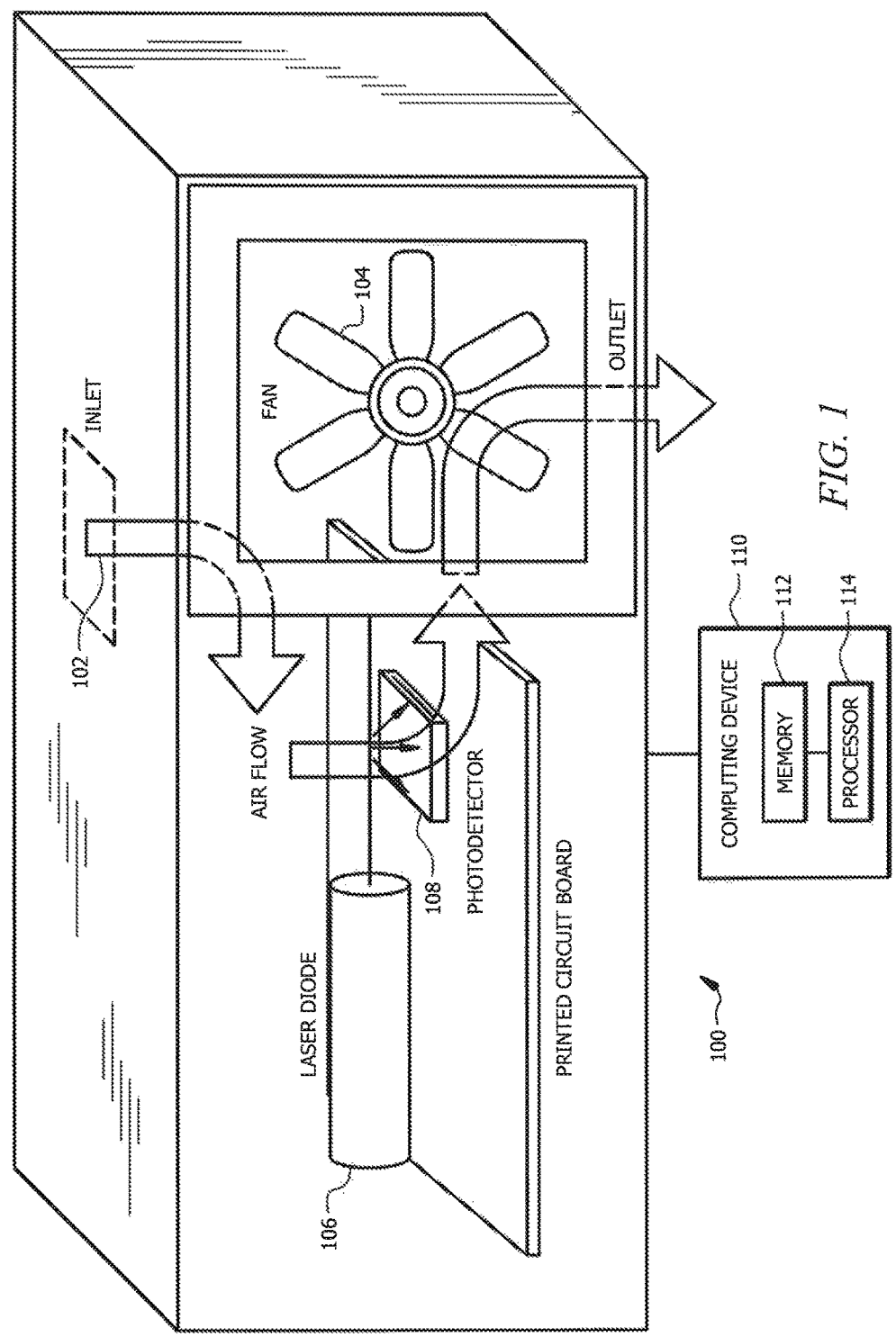
FIG. 1 is an illustration of a dust sensor according to an embodiment of the disclosure.

Systems, methods, and devices for sensing particulate matter are described herein. For example, one or more embodiments include a computing device having a processor and a memory storing instructions which, when executed by the processor, cause the processor to: receive a first plurality of electronic signals from a photodetector over a particular period of time, the first plurality of electronic signals associated with a first plurality of particles, wherein each of the first plurality of signals has a respective amplitude; sort the first plurality of signals into a plurality of amplitude levels; determine a respective quantity of signals associated with each amplitude level; determine an average summation of the first plurality of signals; perform a calibration using the average summation; receive a second plurality of electronic signals from the photodetector over a period of time subsequent to the calibration, the second plurality of electronic signals associated with a second plurality of particles; and determine a mass concentration of the second plurality of particles based on the second plurality of electronic signals.

Particulate matter (sometimes referred to herein as "dust") is a particle pollution that can be a mixture of solids and/or liquid droplets in the air. Some particles can be released directly from a specific source, while others form via complex chemical reactions in the atmosphere. The particulate matter can come in a variety of range sizes, including coarse dust particles and/or fine particles. For example, particles less than or equal to 10 micrometers in diameter are small particles which can enter the lungs, potentially causing serious health problems. Particles less than 2.5 micrometers in diameter ($PM_{2.5}$) may be classified as "fine" particles and may pose the greatest health risks.

Dust sensors in accordance with the present disclosure can provide improved accuracy and/or performance for detecting fine particulate matter (e.g., $PM_{2.5}$) while providing a digital display of meaningful air quality and/or air pollution levels. Embodiments of the present disclosure can provide accuracy, stability, and/or consistency that exceeds those of LED-based sensors. Additionally, embodiments herein can be less costly than previous laser-based sensors.

Embodiments of the present disclosure can provide a reading of mass concentration using a particle matter 2.5 ($PM_{2.5}$) reading. That is, the air quality and/or air pollution can be calculated as a mass concentration of the fine particles. The mass concentration, air quality, and/or pollution can be provided via a digital display, for instance.

Embodiments of the present disclosure can include a laser diode, a photodetector, an air fluid tunnel, and a fan for air flow control. A laser may be used, rather than an LED, because laser light may exhibit increased convergence and/or light intensity. Thus, the light scattered by the dust particles may take the form of a plurality of pulses over a given observation period, whereas LED designs may only receive envelopes of light signals over the observation period, which may be less indicative of an amount of particles in the air. Embodiments herein can include a device, such as a controller and/or computing device, which receives the pulses and transforms information contained in the pulses into mass concentration for digital display.

The present disclosure teaches employing a mass separation fluid tunnel to separate, at least partially, fine particles into a first fluid channel and large particles into a second fluid channel, and performing the determination of particulate matter concentration in the first fluid channel (i.e., on the separated fine particles). This may be accomplished by arranging the first fluid channel to be located vertically above the second fluid channel, whereby the larger particles may precipitate out of the fluid stream and follow the second, lower fluid channel while the finer particles remain suspended and follow the first, upper fluid channel. The second fluid channel may be disposed as a branch that deviates down, away from the first fluid channel, and the first fluid channel may be disposed as a continuation of the path of an unbranched inflow channel. A fluid port that provides communication between the second fluid channel and the first fluid channel may be disposed downstream of the fork or branch and may promote some of the fine particles that chanced to follow the second fluid channel to rise to rejoin the first fluid channel, thereby providing a more accurate determination of the particulate matter concentration in the inflow air.

In an alternative configuration, the mass separation fluid tunnel may comprise a first fluid channel and a second fluid channel that branch off of a single inflow channel. The first fluid channel is exhausted by a first fan, and the second fluid channel is exhausted by a second fan where the second fan is an adjustable speed fan, the speed of which has been adapted by the computing device based on reading a fan speed parameter stored in memory. The speed of the second fan may adapt a mass separation threshold with reference to the size of particles that are separated off into the first fluid channel versus the size of particles that are separated off into the second fluid channel. This alternative may offer several advantages including allowing use of the same manufactured assembly in different systems having different specified particle size measurement capability. This alternative may offer flexibility in orientation of the dust sensor. For example, this alternative may not depend on the vertical alignment of the first channel and the second channel, as the mass separation depends at least partly on the speed of the second fan independently of the orientation to the force of gravity.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of spikes" can refer to one or more spikes.

FIG. 1 illustrates a system 100 for sensing particulate matter in accordance with one or more embodiments of the present disclosure. The system 100 can be (or be a portion of) a particulate matter sensor (alternatively referred to herein as a "dust sensor").

The system 100 can include an air fluid tunnel 102, which is herein referred to as "duct 102." The duct 102 can have an inlet and an outlet, for instance. The system 100 can include a fan 104. The fan 104 can draw air (and particulate matter carried by the air) into the duct 102. The fan 104 can be used to direct the air past a region of the system 100 where the particulate matter is sensed.

The system 100 can include a laser diode 106, referred to herein as "laser 106." The laser 106 can generate a beam of light. In some embodiments, the beam of light can be collimated and/or focused. It is noted that embodiments of the present disclosure do not limit the laser 106 to a particular type of laser. Additionally, though one laser 106 is shown, embodiments of the present disclosure can utilize more than one laser.

The system 100 can include a photodetector 108. The photodetector 108 is a device that receives one or more light signals and transforms the light signal(s) into electronic signal(s). Embodiments of the present disclosure do not limit the photodetector 108 to a particular type of photodetector. In some embodiments, the system 100 can be contained in an enclosure. For instance, the enclosure can be approximately 2 centimeters by 2 centimeters by 1 centimeter in dimension, though embodiments of the present disclosure are not so limited.

Particulate matter in air, herein referred to as "dust", can enter the duct 102, drawn in by the fan 104, for instance. Thereafter, the dust can travel into a path of the beam of the laser 106. The laser beam light can scatter and/or reflect off of the dust. The scattered light signals can be received by the photodetector 108. The photodetector 108 can transform the scattered light signals into electronic signals.

In some embodiments, the laser 106, the fan 104, and/or the photodetector 108 can be controlled by a computing device (e.g., microprocessor) 140. The computing device 110 can execute instructions (e.g., implemented as software and/or firmware) to control the laser 106, the fan 104, and/or the photodetector 108. Further, as discussed herein, the computing device 110 can convert the electronic signals received from the photodetector 108 to determine mass concentration of the dust. The computing device 110 can allow the display of the determined mass concentration. That is, in some embodiments, the system 100 can include a display configured to display a determined mass concentration of dust.

The computing device 110 can include a memory 112. The memory 112 can be any type of storage medium that can be accessed by a processor 114 to perform various examples of the present disclosure. For example, the memory 112 can be a non-transitory computer readable medium having computer readable instructions (e.g., computer program instructions) stored thereon that are executable by the processor 114 to receive a number of electronic signals.

The memory 112 can be volatile or nonvolatile memory. The memory 112 can also be removable (e.g., portable) memory, or non-removable (e.g., internal) memory. For example, the memory 112 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium, such as magnetic cassettes, tapes, or disks, among other types of memory.

Further, although the memory 112 is illustrated as being located within the computing device 110, embodiments of the present disclosure are not so limited. For example, the memory 112 can also be located internal to another computing resource (e.g., enabling computer readable instructions to be downloaded over the Internet or another wired or wireless connection).

In addition, though the computing device 110 is illustrated as being located external to the enclosure housing the duct 102, the fan 104, the laser 106, and the photodetector 108, in some embodiments, the computing device 110 can be located inside (or partially inside) the enclosure.

As previously discussed, the computing device. 110 can receive electronic signals from the photodetector 108. In some embodiments, the computing device 110 can receive a first plurality of electronic signals from the photodetector 108 over a particular period of time, the first plurality of electronic signals associated with a first plurality of particles, wherein each of the first plurality of signals has a respective amplitude. An analog to digital converter (ADC) can be located on a same printed circuit board (PCB) as the photodetector, for instance, and can sample the electronic signals.

Each signal can have a unique shape consisting of a positive voltage crest and a negative voltage crest. Because the ADC is single-ended, for instance, it may only sample voltages above zero. Therefore, there may be a DC offset baseline in between the positive (upward) and negative (downward) crests. The computing device 110 can determine the DC offset by averaging a plurality of samples (received signals) when the laser 106 is turned down to a power level below a particular threshold and the signal is not scattered, for instance. Then, peak values of the signals can be tracked when the signal voltage crosses the DC offset plus a predefined "noise" threshold. In some embodiments, the noise threshold can be determined to be a voltage level that is not exceeded by any noise signals over a particular period of time. If a positive crest and a negative crest are received, and a signal duration threshold is exceeded, the signal can be deemed to be a valid signal representative of a particle. In some embodiments, the signal duration (pulse width) threshold can be set at 50 microseconds. Voltage amplitude information associated with the signal can be determined and stored, for instance.

Computing device 110 can thus determine peak amplitudes of each of the received first plurality of signals. Computing device 110 can sort the first plurality of signals into a plurality of amplitude levels (sometimes referred to as "bins"). The peak amplitudes can be sorted into a plurality of bins, where each bin defines a different range of amplitudes. Signals having relatively small amplitudes may be representative of smaller particles than signals having relatively large amplitudes, for instance.

In some embodiments, a denser classification can be used for smaller pulses due to the greater variation of smaller pulses and/or greater contribution to mass than larger ones. Thus, a first subset of bins associated with smaller pulses (e.g., below a threshold amplitude level) may be separated by a first (e.g., 50 mV) interval, for example, while a second subset of bins associated with larger pulses (e.g., above a threshold amplitude level) may be separated by a second (e.g., 100 mV) interval. In an example, a plurality of bins in accordance with the present disclosure can have upper limits of 30 mV, 50 mV, 100 mV . . . 700 mV, 800 mV, and 1V. In some embodiments, a maximum amplitude threshold level (e.g., 1V) can be set such that signals exceeding the amplitude threshold can be discarded. For example, extremely large particles may impart large, undesirable variations in dust sensing.

Computing device 110 can determine a respective quantity of signals associated with each bin. That is, count of signals falling within each bin can be determined. Each bin can be assigned a value. For example, a first bin with an upper limit of 30 mV can be assigned a value of 1, and a second bin with an upper limit of 50 mV can be assigned a value of 2. The number of signals falling into the bins can be multiplied by the bin value to allow the determination of a signal count number. In the example, 2 pulses falling in the first bin and 2 pulses falling in the second bin would yield a signal count of 6.

Computing device 110 can determine an average summation of the first plurality of signals. In some embodiments, a total summation of all amplitude bins multiplied by the signal count number can be determined. A moving average of that summation can be determined at a particular interval over a particular period of time. In some embodiments, a moving average can be determined every second over a period of ten seconds. This average summation of the first plurality of signals is sometimes referred to herein as "sigma_nv." In a formula, two coefficients can be used: a density factor (k) that relates to average dust density, and a shape coefficient ($\alpha$) that describes particle shape. In some embodiments, the shape coefficient can be set at 1 for ease of calculation. To determine a "fictional" concentration, C, the computing device 110 can multiply sigma_nv by the density factor:

$$C = k \sum_{i=1}^{q} N(v_i) v_i^{\alpha}$$

where N is the signal count and $v_i$ is pulse amplitude.

In some embodiments, computing device 110 can use another moving average over a particular period of time to stabilize the fictional mass concentration. That is, the sigma_nv can be determined every second, for example, over a period of 30 seconds to determine a moving average. A known standard reference, such as a determined concentration in identical settings from another dust sensor (e.g., a reference sensor) known to provide accurate sensing, can be compared with the fictional concentration. Computing device 110 can perform a curve fitting calibration between the fictional concentration and the known (reference) concentration to determine the coefficients in a linear and/or polynomial fashion. Those coefficients can be used to calibrate the sigma_nv to mass concentration and can be stored in the memory 112, for instance, and/or on memory (e.g., EEPROM) of the PCB.

Once calibrated, the system 100 can be used to sense dust. That is, the system 100 can receive a second plurality of electronic signals from the photodetector 108 over a period of time subsequent to the calibration, the second plurality of electronic signals associated with a second plurality of particles, and determine a mass concentration of the second plurality of particles based on the second plurality of electronic signals.

Figure 2:
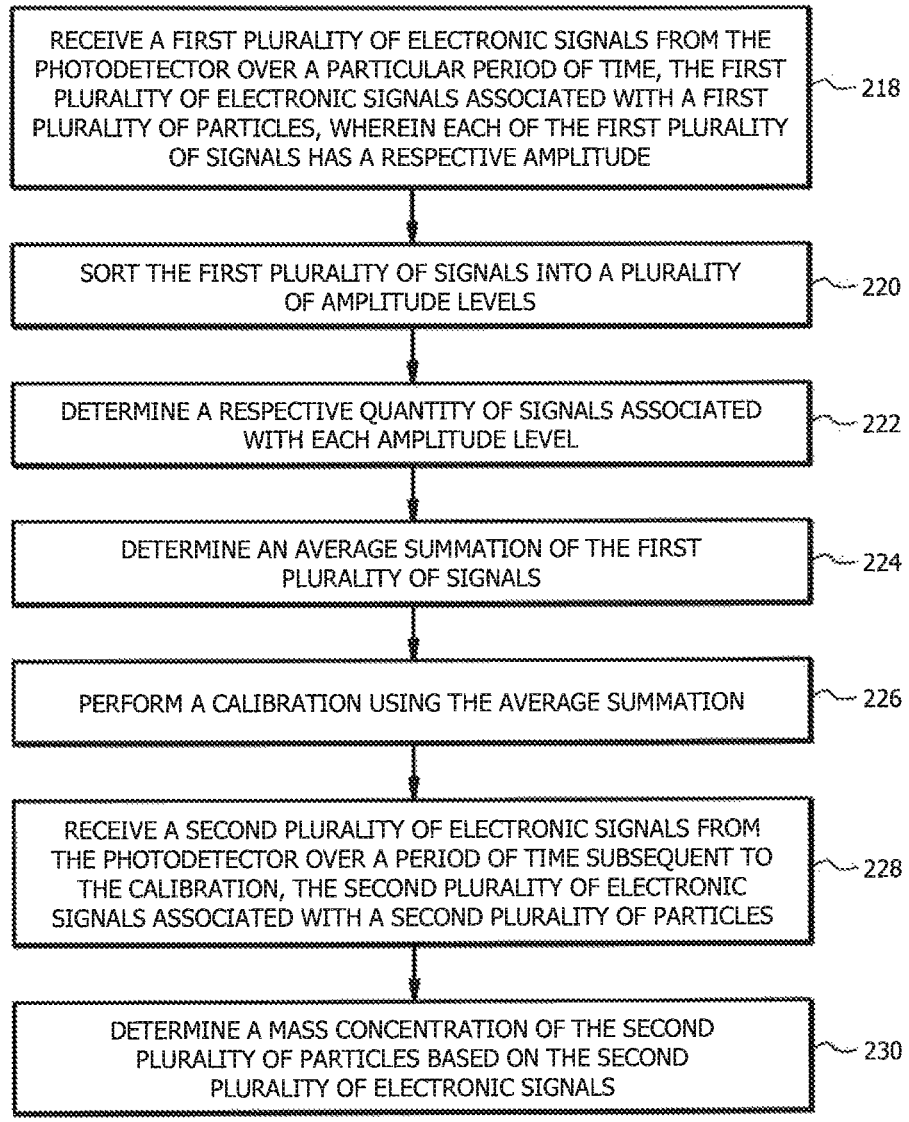
FIG. 2 is a flowchart of a method according to an embodiment of the disclosure.

FIG. 2 illustrates a method 216 for sensing particulate matter in accordance with one or more embodiments of the present disclosure. Method 216 can be performed by a computing device (e.g., computing device 110, previously described in connection with FIG. 1), for instance. Additionally, method 216 can be performed for electronic signals received from a photodetector in a dust sensor 120 as described with reference to FIG. 3 below or in a dust sensor 150 as described with reference to FIG. 4 below.

At block 218, method 216 includes receiving a first plurality of electronic signals from a photodetector over a particular period of time, the first plurality of electronic signals associated with a first plurality of particles, wherein each of the first plurality of signals has a respective amplitude. Each signal can have a unique shape consisting of a positive voltage crest and a negative voltage crest. In some embodiments, there may be a DC offset baseline in between the positive (upward) and negative (downward) crests. Method 216 can include determining the DC offset by averaging a plurality of samples (received signals) when the laser is turned down to a power level below a particular threshold and the signal is not scattered, for instance. Then, peak values of the signals can be tracked when the signal voltage crosses the DC offset plus a predefined "noise" threshold.

At block 220, method 216 includes sorting the first plurality of signals into a plurality of amplitude levels (e.g., bins). The peak amplitudes can be sorted into a plurality of bins, where each bin defines a different range of amplitudes. Signals having relatively small amplitudes may be representative of smaller particles than signals having relatively large amplitudes, for instance.

In some embodiments, a denser classification can be used for smaller pulses due to the greater variation of smaller pulses and/or greater contribution to mass than larger ones. Thus, bins associated with smaller pulses may be separated by a 50 mV interval, for example, while bins associated with larger pulses may be separated by a 100 mV interval. In some embodiments, a maximum amplitude threshold level (e.g., 1V) can be set such that signals exceeding the amplitude threshold can be discarded.

At block 222, method 216 includes determining a respective quantity of signals associated with each amplitude level. Each bin can be assigned a value. For example, a first bin with an upper limit of 30 mV can be assigned a value of 1, and a second bin with an upper limit of 50 mV can be assigned a value of 2. The number of signals falling into the bins can be multiplied by the bin value to allow the determination of a signal count number. In the example, 2 pulses falling in the first bin and 2 pulses falling in the second bin would yield a signal count of 6.

At block 224, method 216 includes determining an average summation of the first plurality of signals. In some embodiments, a total summation of all amplitude bins multiplied by the signal count number can be determined. A moving average of that summation can be determined at a particular interval over a particular period of time. In some embodiments, a moving average can be determined every second over a period of ten seconds. As previously discussed, this average summation of the first plurality of signals can be referred to as "sigma_nv."

At block 226, method 216 includes performing a calibration using the average summation. A curve fitting calibration can be performed between the fictional concentration and the known (reference) concentration to determine coefficients in a linear and/or polynomial fashion. Those coefficients can be used to calibrate the sigma_nv to mass concentration and can be stored in memory, for instance (e.g., EEPROM of the PCB).

At block 228, method 216 includes receiving a second plurality of electronic signals from the photodetector over a period of time subsequent to the calibration, the second plurality of electronic signals associated with a second plurality of particles. Once calibrated, the system can be used to sense dust. That is, the system can receive a second plurality of electronic signals from the photodetector over a period of time subsequent to the calibration, the second plurality of electronic signals associated with a second plurality of particles. At block 230, method 216 includes determining a mass concentration of the second plurality of particles based on the second plurality of electronic signals. Such determination can be carried out in a manner analogous to the determination of the first plurality of particles using the determined coefficients, for instance.

Figure 3:
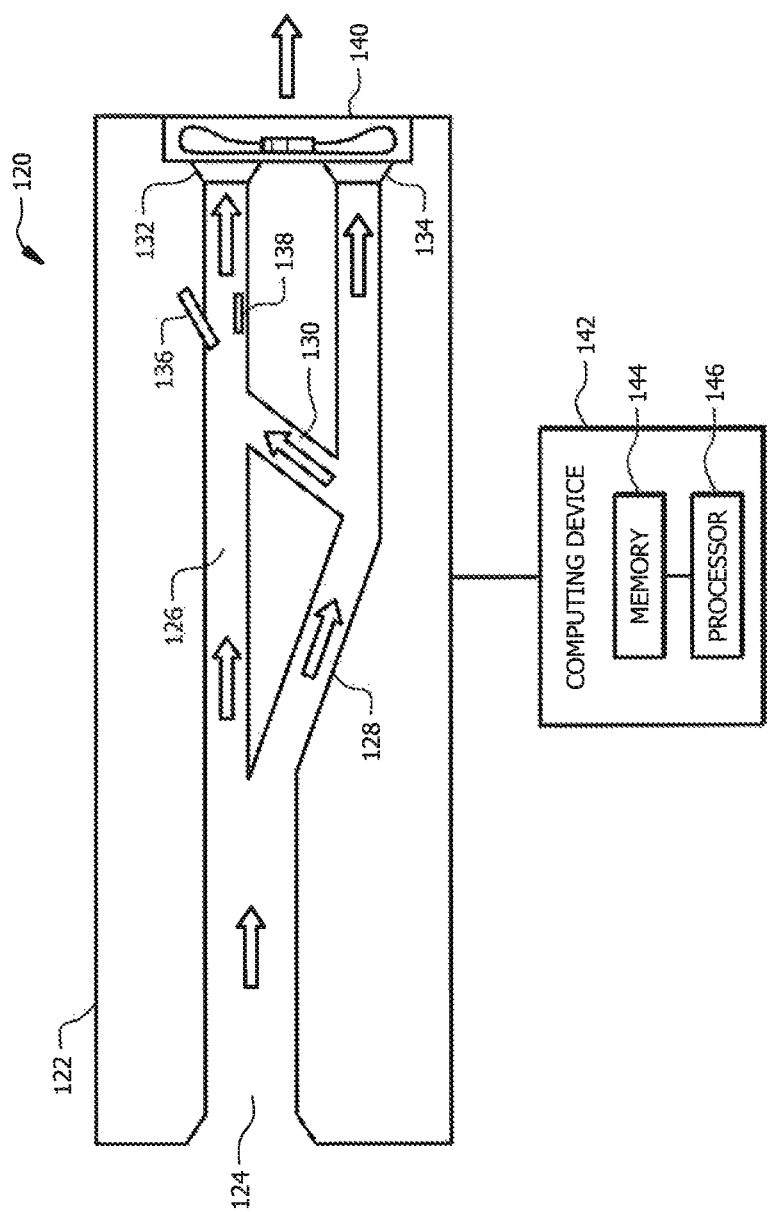
FIG. 3 is an illustration of another dust sensor according to an embodiment of the disclosure.

Turning now to FIG. 3, a dust sensor 120 is described. Portions of the sensor 120 are consistent with the system 100 and method 216 described above. The dust sensor 120, however, features some distinctive elaborations and refinements with reference to using fluid channel branches to encourage mass separation of particulate matter. As an example, in an embodiment, it may be desirable to measure a particulate matter concentration in a fluid containing dust particles of 2.5 micron diameter or less, exclusive of larger particles. For example, cleaned air at the inlet and/or the outlet of a domestic air cleaner appliance may be sensed to detect a particulate matter concentration of dust particles of 2.5 micron diameter less. To promote this object, the fluid air stream may have larger diameter particles separated out or removed from the fluid air stream that passes over a photodetector. It is understood that the mass separation may reduce rather than completely eliminate the presence of larger diameter particles in the fluid stream that passes over the photodetector. In are embodiment, the speed of the fan 140 may be calibrated at manufacture or during maintenance to adapt the particle size of mass separation.

The dust sensor 120 comprises a mass separation fluid tunnel 122. The tunnel 122 comprises a fluid inflow channel 124 that branches into a first fluid channel branch 126 and a second fluid channel branch 128. In use, a fluid enters the mass separation fluid tunnel 122 from the left, into the fluid inflow channel 124 and splits to flow partially through the first fluid channel branch 126 and to flow partially through the second fluid channel branch 128. The fluid stream in the first fluid channel branch 126 exits through a first outlet 132, and the fluid stream in the second fluid channel branch 128 exits through a second outlet 134. In an embodiment, the first fluid channel branch 126 may continue in a direction that is the same as the direction of the fluid inflow channel 124. Said in other words, the first fluid channel branch 126 may be substantially coaxial with the fluid inflow channel 124. In an embodiment, a cross-sectional area of the first fluid channel branch 126 may be about equal to a cross-sectional area of the fluid inflow channel 124. In an embodiment, the second fluid channel branch 128 turns away from and makes an angle (at least at an initial branching off point) with the fluid inflow channel 124. The mass separation fluid tunnel 122 further comprises a fluid port 130 that promotes fluid communication between the first fluid channel branch 126 and the second fluid channel branch 128.

The mass separation fluid tunnel 122 may be referred to as a mass separation fluid tunnel body that defines the inflow channel 124, the first fluid channel branch 126, the second fluid channel branch 128, and the fluid port 130 as interior cavities or channels. The mass separation fluid tunnel body may be formed of any suitable material, such as plastic, metal, ceramic, or other material. The mass separation fluid tunnel body may be less than 3 cm by 3 cm by 1.5 cm in size. The inflow channel 124, the first fluid channel branch 126, the second fluid channel branch 128, and the fluid port 130 may be formed by drilling, lathing, by injection molding, and/or by another process.

In an embodiment, in use, the dust sensor 120 desirably is oriented so that the axis of the first fluid channel branch 126 is above the second fluid channel branch 128. In this orientation, larger particles in the inflowing fluid stream may be encouraged to precipitate out of the fluid stream and hence be concentrated in a branch of the fluid stream that flows into the second fluid channel branch 128. In use, a fan 140 operates to expel fluid, for example air, from the fluid tunnel 122 which induces inflow of the fluid into the fluid inflow channel 124 at the left in FIG. 3. Some of the fine particulate matter in the fluid stream may be carried into the second fluid channel branch 128. The fluid port 130 provides an opportunity to lift at least some of the fine particulate matter in the second fluid channel branch 128 to the first fluid channel branch 126, which may improve the accuracy of the determination of the concentration of fine particles in the fluid.

A light source 136, for example, a laser diode, radiates light into the fluid flowing in the first fluid channel branch 126. The light scatters off the particles suspended and carried in the fluid flowing in the first fluid channel branch 126 and is detected by the photodetector 138. When there are more particles present, the photodetector 138 detects more scattered light. A computing device 142 comprising a memory 144, and a processor 146 receives and processes the output of the photodetector 138.

Figure 4:
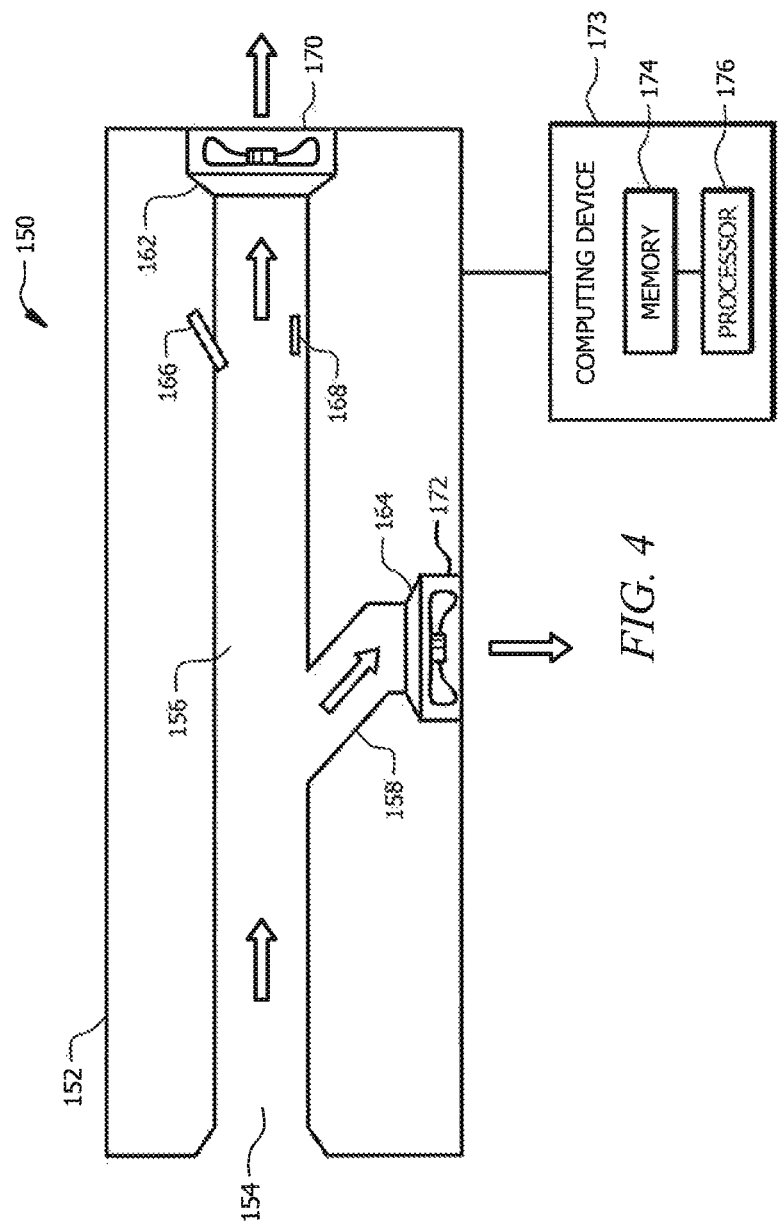
FIG. 4 is an illustration of yet another dust sensor according to an embodiment of the disclosure.

Turning now to FIG. 4, a second dust sensor 150 is described. Portions of the second dust sensor 150 are consistent with the system 100 and method 216 described above. The second dust sensor 150, however, features some distinctive elaborations and refinements with reference to using fluid channel branches to encourage mass separation of particulate matter in the fluid flowing over the photodetector. The second sensor comprises a mass separation fluid tunnel 152, a fluid inflow channel 154, a first fluid channel branch 156 having a first outlet 162, a second fluid channel branch 158 having a second outlet 164, a fan 170, and an adjustable speed tan 172. The second sensor 150 further comprises a light source 166, a photodetector 168, and a computing device 173. The computing device 173 comprises a memory 174 and a processor 176. The second mass separation fluid tunnel 152 may be referred to as a mass separation fluid tunnel body that defines the inflow channel 154, the first fluid channel branch 156, and the second fluid channel branch 158 as interior cavities or channels. The mass separation fluid tunnel body may be formed of any suitable material, such as plastic, metal, ceramic, or other material. The mass separation fluid tunnel body may be less than 3 cm by 3 cm by 1.5 cm in size. The inflow channel 154, the first fluid channel branch 156, and the second fluid channel branch 158 may be formed by drilling, lathing, injection molded, and/or by another process.

Similarly to the sensor 120 described above with reference to FIG. 3, the fluid enters the mass separation fluid tunnel from the left and enters the fluid inflow channel 154. The fluid inflow channel 154 branches off as the first fluid channel branch 156 and the second fluid channel branch 158. Some of the fluid in the fluid inflow channel 154 flows into the first fluid channel branch 156 and the remainder flows into the second fluid channel branch 158. The fan 170 exhausts the fluid exiting the first outlet 162, and the adjustable speed fan 172 exhausts the fluid exiting the second outlet 164. The combined effect of the fan 170 and the adjustable speed fan 172 is to draw in fluid from the left into the fluid inflow channel 154.

By adapting the speed of the adjustable speed fan 172, the mass distribution of particles in each of the first fluid channel branch 156 and the second fluid channel branch 158 may be selected. In an embodiment, a fan speed parameter is stored in the memory 174. The computing device 173 reads the fan speed parameter value and sets the speed control input of the adjustable speed fan 172 accordingly. In an embodiment, the adjustable speed fan 172 is controlled with pulse width modulation (PWM) inputs from the computing device 173 and provides a speed output to the computing device 173 as feedback. The fan speed parameter may be written to during manufacturing of the sensor 150 to adapt the sensor to a specific application and/or specification. In an embodiment, the fan speed parameter may be written to by the computing device 173, for example, by the processor 176. In some contexts, the fan speed parameter may be said to be reprogrammable or reconfigurable.

The dust sensor 150 having the adjustable speed fan 172 can be used in different fluid handling systems with no other alteration than altering the value stored in the fan speed parameter. Said in another way, a generic dust sensor 150 may be applied in different fluid handling systems that have different specifications. This may reduce the number of parts to be stocked by a manufacturer of fluid handling systems. In an embodiment, the dust sensor 150 may also be mounted in a fluid handling system without regard to alignment with the direction of gravity.

In an embodiment, a plurality of dust sensors 150 may be coupled together for measuring concentration of different sizes of particulate matter in a fluid. For example, a first sensor 150 may be configured (i.e., the fan speed parameter programmed to adapt the adjustable speed fan 172 accordingly) to separate particulate matter larger than 10 microns into the second fluid channel branch 158 and measure the concentration of particulate matter 10 microns and below in the first fluid channel branch 156. The outflow of the first fluid channel branch 156 of the first sensor 150 may feed the fluid inflow channel 154 of a second sensor 150. The second sensor 150, for example, may be configured (i.e., the fan speed parameter programmed to adapt the adjustable speed fan 172 accordingly) to separate particulate matter larger than 5 microns into the second fluid channel branch 158 and measure the concentration of particulate matter 5 microns and below in the first fluid channel branch 156. The outflow of the first fluid channel branch 156 of the second sensor 150 may feed the fluid inflow channel 154 of a third sensor 150. The third sensor 150, for example, may be configured (i.e., the fan speed parameter programmed to adapt the adjustable speed fan 172 accordingly) to separate particulate matter larger than 2.5 microns into the second fluid channel branch 158 and measure the concentration of particulate matter 2.5 microns and below in the first fluid channel branch 156. The particulate concentration values determined by the first, second, and third sensor 150 may be used in combination to determine mass concentrations of different ranges of particle sizes.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion and not a restrictive one. Combination of the above embodiments and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A particulate matter (PM) sensor, comprising:
    a mass separation fluid tunnel body defining a fluid inflow channel, a first fluid channel branch opening off of the inflow channel and having a first outlet, a second fluid channel branch opening off of the inflow channel and having a second outlet, and a fluid port between the first fluid channel branch and the second fluid channel branch;
    a fan located downstream of the first outlet and the second outlet;
    a photodetector located in the first fluid channel branch; and
    a computing device coupled to the photodetector having a processor and a memory storing instructions which, when executed by the processor, determines a mass concentration of particles in the first fluid channel branch based on an output of the photodetector.

2. The particulate matter sensor of claim 1, wherein the photodetector is located downstream of the fluid port in the first fluid channel branch.

3. The particulate matter sensor of claim 1, wherein the photodetector is configured to detect light scattered off of particulate matter in a fluid stream in first fluid channel branch.

4. The particulate matter sensor of claim 1, wherein the mass separation fluid tunnel body is less than about 3 cm by 3 cm by 1.5 cm in size.

5. The particulate matter sensor of claim 1, wherein the sensor is a dust sensor.

6. The particulate matter sensor of claim 1, further comprising a light source.

7. The particulate matter sensor of claim 6, wherein the light source is a laser diode.

8. The particulate matter sensor of claim 1, wherein the first fluid channel branch continues the path of the fluid inflow channel.

9. The particulate matter sensor of claim 8, wherein the second fluid channel branch diverges from the fluid inflow channel.

10. A particulate matter (PM) sensor, comprising:
    a mass separation fluid tunnel body defining a fluid inflow channel, a first fluid channel branch opening off of the inflow channel and having a first outlet, a second fluid channel branch opening off of the inflow channel and having a second outlet, and a fluid port between the first fluid channel branch and the second fluid channel branch;
    a fan located downstream of the first outlet and the second outlet;
    a laser diode;
    a photodetector located in the first fluid channel branch; and
    a computing device coupled to the photodetector having a processor and a memory storing instructions which, when executed by the processor, determines a mass concentration of particles in the first fluid channel branch based on an output of the photodetector, where the output of the photodetector is based on detecting light emitted by the laser diode scattered by dust particles present in a fluid flow through the first fluid channel branch.

11. The particulate matter sensor of claim 10, wherein the sensor is a dust sensor.

12. The particulate matter sensor of claim 10, wherein the second fluid channel branch diverges from the fluid inflow channel.

13. The particulate matter sensor of claim 10, therein an operating speed of the fan is calibrated to separate particulate matter larger than about 2.5 microns to follow the second fluid channel branch and separate particulate matter of about 2.5 microns and smaller to follow the first fluid channel branch.

* * * * *